US00PP29172P2

(12) United States Plant Patent
Arts

(10) Patent No.: US PP29,172 P2
(45) Date of Patent: Apr. 3, 2018

(54) ***HYDRANGEA* PLANT NAMED 'HBA215909'**

(50) Latin Name: *Hydrangea macrophylla*
Varietal Denomination: HBA215909

(71) Applicant: Niels Arts, Aalsmeer (NL)

(72) Inventor: Niels Arts, Aalsmeer (NL)

(73) Assignee: Hydrangea Breeders Association B.V., De Kwakel (NL)

( * ) Notice: Subject to any disclaimer, the term of this patent is extended or adjusted under 35 U.S.C. 154(b) by 0 days.

(21) Appl. No.: 15/530,483

(22) Filed: Jan. 20, 2017

(51) Int. Cl.
*A01H 5/02* (2018.01)

(52) U.S. Cl.
USPC ..... Plt./250

(58) Field of Classification Search
USPC ..... Plt./250
See application file for complete search history.

(56) References Cited

PUBLICATIONS

PLUTO Plant Variety Database Dec. 21, 2017. p. 1.*

* cited by examiner

*Primary Examiner* — Annette H Para
(74) *Attorney, Agent, or Firm* — C. A. Whealy

(57) ABSTRACT

A new and distinct cultivar of *Hydrangea* plant named 'HBA215909', characterized by its upright and rounded plant habit; vigorous growth habit; rapid growth rate; freely branching habit with strong, thick and sturdy stems; freely and uniformly flowering habit; mophead-type inflorescences with numerous white-colored sterile flowers; and good post-production longevity.

2 Drawing Sheets

Botanical designation: *Hydrangea macrophylla.*
Cultivar denomination: 'HBA215909'.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'HBA215909'.

The new *Hydrangea* plant is a product of a planned breeding program conducted by the Inventor in De Kwakel, The Netherlands. The objective of the breeding program was to create new freely-branching *Hydrangea* plants with strong sturdy stems, large inflorescences, attractive flower color and good postproduction longevity.

The new *Hydrangea* plant originated from a cross-pollination made by the Inventor in September, 2011 in De Kwakel, The Netherlands, of a proprietary selection of *Hydrangea macrophylla* identified as code number 617, not patented, as the female, or seed, parent with a proprietary selection of *Hydrangea macrophylla* identified as code number 03-0124-011, not patented, as the male, or pollen, parent. The new *Hydrangea* plant was discovered and selected by the Inventor as a single flowering plant from within the progeny of the stated cross-pollination in a controlled greenhouse environment in De Kwakel, The Netherlands in March, 2012.

Asexual reproduction of the new *Hydrangea* plant by vegetative cuttings in a controlled environment in De Kwakel, The Netherlands since September, 2012 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HBA215909'. These characteristics in combination distinguish 'HBA215909' as a new and distinct *Hydrangea* plant:

1. Upright and rounded plant habit.
2. Vigorous growth habit and rapid growth rate.
3. Freely branching habit with strong, thick and sturdy stems.
4. Freely and uniformly flowering habit.
5. Mophead-type inflorescences with numerous white-colored sterile flowers.
6. Good postproduction longevity.

Plants of the new *Hydrangea* can be compared to plants of the female parent selection. Plants of the new *Hydrangea* differ primarily from plants of the female parent selection in sterile flower sepal color as plants of the female parent selection have light pink-colored sterile flower sepals.

Plants of the new *Hydrangea* can be compared to plants of the male parent selection. Plants of the new *Hydrangea* differ primarily from plants of the male parent selection in sterile flower sepal size as plants of the new *Hydrangea* have larger sterile flower sepals than plants of the male parent selection.

Plants of the new *Hydrangea* can be compared to plants of the *Hydrangea hybrida* 'Agrihydranegen', disclosed in U.S. Plant Pat. No. 23,783. In side-by-side comparisons conducted in De Kwakel, The Netherlands, plants of the new *Hydrangea* differ from plants of 'Agrihydranegen' in the following characteristics:

1. Plants of the new *Hydrangea* are more uniform than plants of 'Agrihydranegen'.

2. Plants of the new *Hydrangea* have larger inflorescences than plants of 'Agrihydranegen'.
3. Plants of the new *Hydrangea* have larger sterile flowers than plants of 'Agrihydranegen'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a side perspective view of a typical flowering plant of 'HBA215909'.

The photograph on the second sheet is a close-up view of a typical inflorescence of 'HBA215909'.

DETAILED BOTANICAL DESCRIPTION

Plants used in the aforementioned photographs and in the following description were grown during the late spring in 15-cm containers in a glass-covered greenhouse in De Kwakel, The Netherlands and under cultural practices typical of commercial *Hydrangea* production. During the production of the plants, day and night temperatures averaged 17° C. Plants of the new *Hydrangea* were pinched one time and were one year old when the photographs and description were taken. Plants of the new *Hydrangea* are not typically treated with aluminum sulfate to "blue" the inflorescences. In the following description, color references are made to The Royal Horticultural Society Colour Chart, 1995 Edition, except where general terms of ordinary dictionary significance are used.

Botanical description: *Hydrangea macrophylla* 'HBA215909'.

Parentage:

*Female, or seed, parent*.—Proprietary selection of *Hydrangea macrophylla* identified as code number 617, not patented.

*Male, or pollen, parent*.—Proprietary selection of *Hydrangea macrophylla* identified as code number 03-0124-011, not patented.

Propagation:

*Type cutting*.—By vegetative cuttings.

*Time to initiate roots, summer*.—About two weeks at temperatures about 23° C.

*Time to initiate roots, winter*.—About 18 days at temperatures about 18° C.

*Time to produce a rooted young plant, summer*.—About four weeks at temperatures about 23° C.

*Time to produce a rooted young plant, winter*.—About five weeks at temperatures about 18° C.

*Root description*.—Thick; typically whitish brown in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Upright and rounded plant habit; strong and sturdy stems; rapid growth rate and vigorous growth habit.

*Plant height*.—About 25 cm to 30 cm.

*Plant diameter or area of spread*.—About 35 cm.

Lateral branch description:

*Branching habit*.—Freely branching habit; when pinched, about nine lateral branches develop per plant.

*Length*.—About 15 cm to 18 cm.

*Diameter*.—About 4 mm to 5 mm.

*Internode length*.—About 2.5 cm to 3 cm.

*Texture*.—Smooth, glabrous.

*Aspect*.—Upright to about 20° from vertical.

*Strength*.—Strong, sturdy.

*Color*.—Close to 144B; at internodes, close to 187A, lenticels, close to 187A.

Leaf description:

*Arrangement*.—Opposite, simple.

*Length*.—About 9 cm to 11 cm.

*Width*.—About 7 cm to 8 cm.

*Shape*.—Ovate.

*Apex*.—Acute.

*Base*.—Obtuse.

*Margin*.—Dentate to serrate.

*Texture, upper surface*.—Smooth to rugose, glabrous.

*Texture, lower surface*.—Rugose, glabrous.

*Venation pattern*.—Pinnate.

*Color*.—Developing leaves, upper surface: Close to 147A. Developing leaves, lower surface: Close to 137C. Fully developed leaves, upper surface: Close to 147B; venation, close to 145B. Fully developed leaves, lower surface: Close to 137C; venation, close to 145D.

*Petioles*.—Length: About 1 cm to 1.5 cm. Diameter: About 3 mm to 4 mm. Texture, upper and lower surfaces: Smooth, glabrous. Color, upper and lower surfaces: Close to 145B.

Flower description:

*Flower type and habit*.—Showy sterile flowers and small, inconspicuous star-shaped fertile flowers arranged on mophead-type terminal panicles; panicles globular in shape; flowers face upright to outwardly depending on the position in the inflorescence.

*Fragrance*.—None detected.

*Natural flowering season*.—Plants begin flowering about one year after planting; flowering is continuous during the summer in Northern Europe.

*Flower longevity*.—Sterile flowers last about four months on the plant, sterile flowers persistent; fertile flowers last about one month on the plant, fertile flowers not persistent.

*Quantity of flowers*.—Freely flowering habit; about 70 to 80 sterile flowers per panicle and about 30 fertile flowers per panicle.

*Panicle height*.—About 8 cm to 10 cm.

*Panicle diameter*.—About 14 cm to 18 cm.

*Sterile flower buds*.—Length: About 3 mm. Diameter: About 3 mm. Shape: Spherical. Color: Close to 155A.

*Fertile flower buds*.—Length: About 3.5 mm. Diameter: About 3 mm. Shape: Spherical. Color: Close to 145A.

*Sterile flower diameter*.—About 3.5 cm to 4 cm.

*Sterile flower depth (height)*.—About 1 cm.

*Fertile flower diameter*.—About 5 mm.

*Fertile flower depth (height)*.—About 5 mm.

*Petals, fertile flowers only, sterile flowers without petals*.—Quantity and arrangement: Five in a single whorl. Length: About 6 mm. Width: About 3 mm. Shape: Ovate. Apex: Acute. Base: Attenuate. Margin: Entire. Texture, upper and lower surfaces: Smooth, glabrous. Color: When opening, upper and lower surfaces: Close to 145D. Fully opened, upper and lower surfaces: Close to 155D; color does not change with development.

*Sepals, sterile flowers*.—Quantity and arrangement: Four in a single whorl. Length: About 1.8 cm to 2 cm. Width: About 3 cm to 3.5 cm. Shape: Deltoid. Apex: Obtuse. Base: Obtuse. Margin: Entire to slightly crenate. Texture, upper and lower surfaces: Smooth, glabrous. Color: When opening, upper and lower surfaces: Close to 145C. Fully opened, upper and lower surfaces: Close to 155B; color does not change with development.

*Sepals, fertile flowers*.—Quantity and arrangement: Five in a single whorl. Length: About 3 mm. Width: About 1.5 mm to 2 mm. Shape: Ovate. Apex: Acute. Base: Obtuse. Margin: Entire. Texture, upper and lower surfaces: Smooth, glabrous. Color: When opening, upper and lower surfaces: Close to 145B. Fully opened, upper and lower surfaces: Close to 145B; color does not change with development.

*Pedicels, sterile flowers*.—Length: About 1.5 cm to 2.5 cm. Diameter: About 2 mm to 4 mm. Strength: Strong. Aspect: Erect to about 45° from vertical. Texture: Smooth, glabrous. Color: Close to 157C.

*Pedicels, fertile flowers*.—Length: About 8 mm. Diameter: About 2 mm to 3 mm. Strength: Strong. Aspect: Mostly upright. Texture: Smooth, glabrous. Color: Close to 157B.

*Reproductive organs, fertile flowers only; sterile flowers without reproductive organs*.—Stamens: Quantity per flower: Eight. Filament length: About 1 mm. Filament color: Close to 155D. Anther shape: Conical. Anther length: About 1 mm. Anther color: Close to 155B. Pollen amount: Abundant. Pollen color: Close to 155D. Pistils: Pistil quantity per flower: Three. Pistil length: About 3 mm. Stigma shape: Oval. Stigma color: Close to 150D. Style length: About 2 mm to 3 mm. Style color: Close to 155B. Ovary color: Close to 155B.

*Seeds*.—Quantity per flower: About 20 to 30. Length: About 0.5 mm. Diameter: About 0.2 mm. Color: Close to 200C.

Disease & pest resistance: Under commercial production conditions, plants of the new *Hydrangea* have not been observed to be resistant to pathogens and pests common to *Hydrangea* plants.

Temperature tolerance: Plants of the new *Hydrangea* have been shown to be tolerant to temperatures ranging from about 3° C. to about 38° C.

It is claimed:

1. A new and distinct *Hydrangea* plant named 'HBA215909' as illustrated and described.

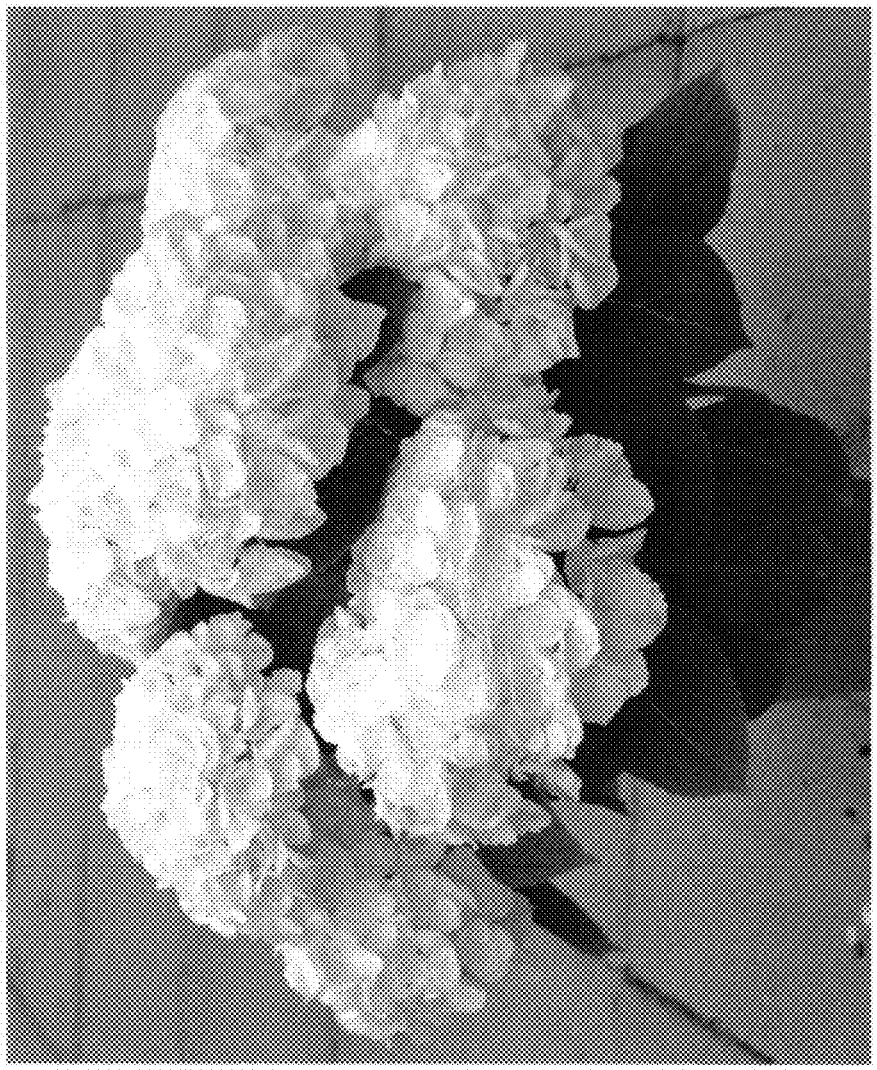

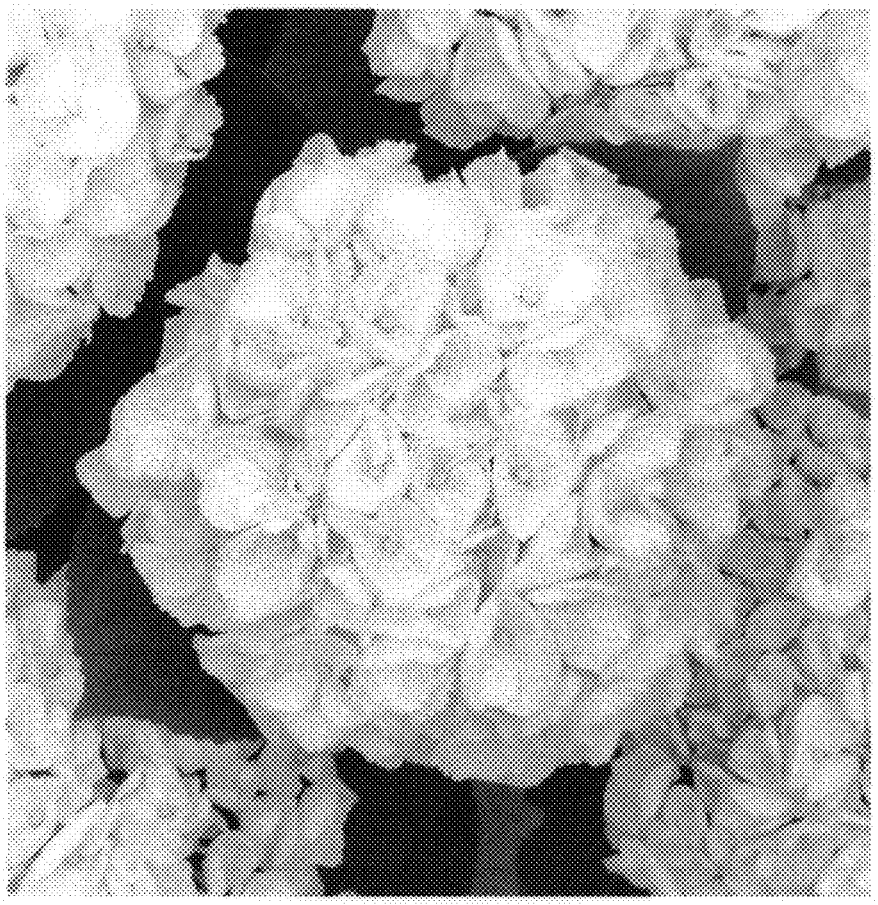

* * * * *